(12) United States Patent
Mantell

(10) Patent No.: US 10,918,813 B2
(45) Date of Patent: Feb. 16, 2021

(54) CARBOXY THERAPY APPLICATOR

(71) Applicant: Northgate Technologies Inc., Elgin, IL (US)

(72) Inventor: Robert R. Mantell, Arlington Heigts, IL (US)

(73) Assignee: NORTHGATE TECHNOLOGIES INC., Elgin, IL (US)

( * ) Notice: Subject to any disclaimer, the term of this patent is extended or adjusted under 35 U.S.C. 154(b) by 279 days.

(21) Appl. No.: 15/906,684

(22) Filed: Feb. 27, 2018

(65) Prior Publication Data

US 2018/0280635 A1    Oct. 4, 2018

Related U.S. Application Data

(63) Continuation of application No. 14/823,529, filed on Aug. 11, 2015, now Pat. No. 9,937,304, which is a (Continued)

(51) Int. Cl.
*A61M 13/00* (2006.01)
*A61M 37/00* (2006.01)
(Continued)

(52) U.S. Cl.
CPC .......... *A61M 13/003* (2013.01); *A61M 5/20* (2013.01); *A61M 16/108* (2014.02); *A61M 37/00* (2013.01); *A61M 16/16* (2013.01); *A61M 16/161* (2014.02); *A61M 2016/0027* (2013.01); *A61M 2016/0033* (2013.01);
(Continued)

(58) Field of Classification Search
CPC .. A61M 13/003; A61M 16/108; A61M 16/16; A61M 16/161; A61M 2016/0027; A61M 2016/0033; A61M 2016/103; A61M 2202/0225; A61M 2205/3324; A61M 2205/3327; A61M 2205/3334; A61M 2205/3358; A61M 2205/3368; A61M 2205/7518; A61M 2205/7527; A61M 2205/7545; A61M 37/00; A61M 5/20; A61M 2016/003
See application file for complete search history.

(56) References Cited

U.S. PATENT DOCUMENTS

| | | | |
|---|---|---|---|
| 5,398,676 A * | 3/1995 | Press ................. | A61M 16/0051 128/204.18 |
| 5,549,546 A * | 8/1996 | Schneider ........... | A61M 13/003 604/23 |

(Continued)

*Primary Examiner* — Quynh-Nhu H. Vu
(74) *Attorney, Agent, or Firm* — Brinks Gilson & Lione

(57) ABSTRACT

Handheld carboxy therapy applicators are disclosed. In one implementation, a handheld carboxy therapy applicator includes a heater module, a humidification module, and a hypodermic needle. The heater module is configured to receive a flow of gas and to warm gas within the flow of gas. The humidification module is in fluid communication, such as in a serial connection, with the heater module. The humidification module is configured to receive the flow of gas from the heater module and to humidify the gas within the flow of gas. The hypodermic needle is in serial connection with the humidification module. The hypodermic needle is configured to receive the flow of gas from the humidification module and to inject the flow of gas into a tissue of a patient.

9 Claims, 15 Drawing Sheets

Related U.S. Application Data continuation of application No. 13/619,310, filed on Sep. 14, 2012, now Pat. No. 9,132,245.

(60) Provisional application No. 61/535,613, filed on Sep. 16, 2011.

(51) Int. Cl.
*A61M 5/20* (2006.01)
*A61M 16/10* (2006.01)
*A61M 16/00* (2006.01)
*A61M 16/16* (2006.01)

(52) U.S. Cl.
CPC .............. *A61M 2016/103* (2013.01); *A61M 2202/0225* (2013.01); *A61M 2205/3324* (2013.01); *A61M 2205/3327* (2013.01); *A61M 2205/3334* (2013.01); *A61M 2205/3358* (2013.01); *A61M 2205/3368* (2013.01); *A61M 2205/7518* (2013.01); *A61M 2205/7527* (2013.01); *A61M 2205/7545* (2013.01)

(56) References Cited

U.S. PATENT DOCUMENTS

| | | | |
|---|---|---|---|
| 6,402,714 B1* | 6/2002 | Kraft-Kivikoski | A61M 13/003 600/560 |
| 2009/0240192 A1* | 9/2009 | Power | B05B 7/0075 604/26 |
| 2013/0087143 A1* | 4/2013 | Pujol | A61M 16/205 128/203.12 |

* cited by examiner

CARBOXY THERAPY APPLICATOR

RELATED APPLICATION

The present application is a continuation of U.S. patent application Ser. No. 14/823,529 (still pending), filed Aug. 11, 2015, which is a continuation of U.S. patent application Ser. No. 13/619,310 (now U.S. Pat. No. 9,132,245), filed Sep. 14, 2012, which claims priority to U.S. Provisional Patent Appln. No. 61/535,613, filed Sep. 16, 2011, the entirety of each of which are hereby incorporated by reference.

BACKGROUND

Under carboxy therapy, carbon dioxide is infused into human tissue for therapeutic purposes, including, without limitation, for reducing stretch marks; reducing cellulite; firming sagging tissues around the neck or buttocks; and reducing wrinkled skin around the eyes and breasts. The basis for the treatment is that carbon dioxide is injected beneath the surface of the skin to cause the body to interpret the cell structure as having an oxygen defect. The body responds by trying to increase blood flow and growth factors or vascular endothelial growth factors (VEGF) in the affected area, thereby encouraging collagen growth and/or causing the body to attack fat tissue.

Currently available carboxy therapy products heat gas at a control unit. While the gas may be heated as it leaves the control unit, the gas may cool to ambient room temperature as it travels through a tube or a series of tubes from the control unit to a hypodermic needle where the gas is injected into the patient. Accordingly, there is a need for improved carboxy therapy products that are able to provide warmed gases to a patient.

DETAILED DESCRIPTION OF THE DRAWINGS

The present disclosure is directed to improved carboxy therapy applicators that are able to provide a desired gas, including, without limitation, carbon dioxide, at a desired flow rate, warmed and/or humidified and/or otherwise conditioned or treated, to a patient for subcutaneous cosmetic purposes. The gas is preferably provided at a range of temperatures being close to body temperature, from 95 to 105 degrees Fahrenheit. Other temperatures ranges may be suitable depending on the particular application, including, without limitation, 75 to 95 degrees Fahrenheit. In some implementations, the desired gas flow rate is within the range of 20 to 150 milliliters per minute. Additionally, the disclosed carboxy therapy applicators, control box, and/or insufflator allow a user, such as a physician, to condition and/or treat the gas and control gas flow, gas pressure, gas temperature, gas humidity, the pH level, and other parameters.

Figure 1:
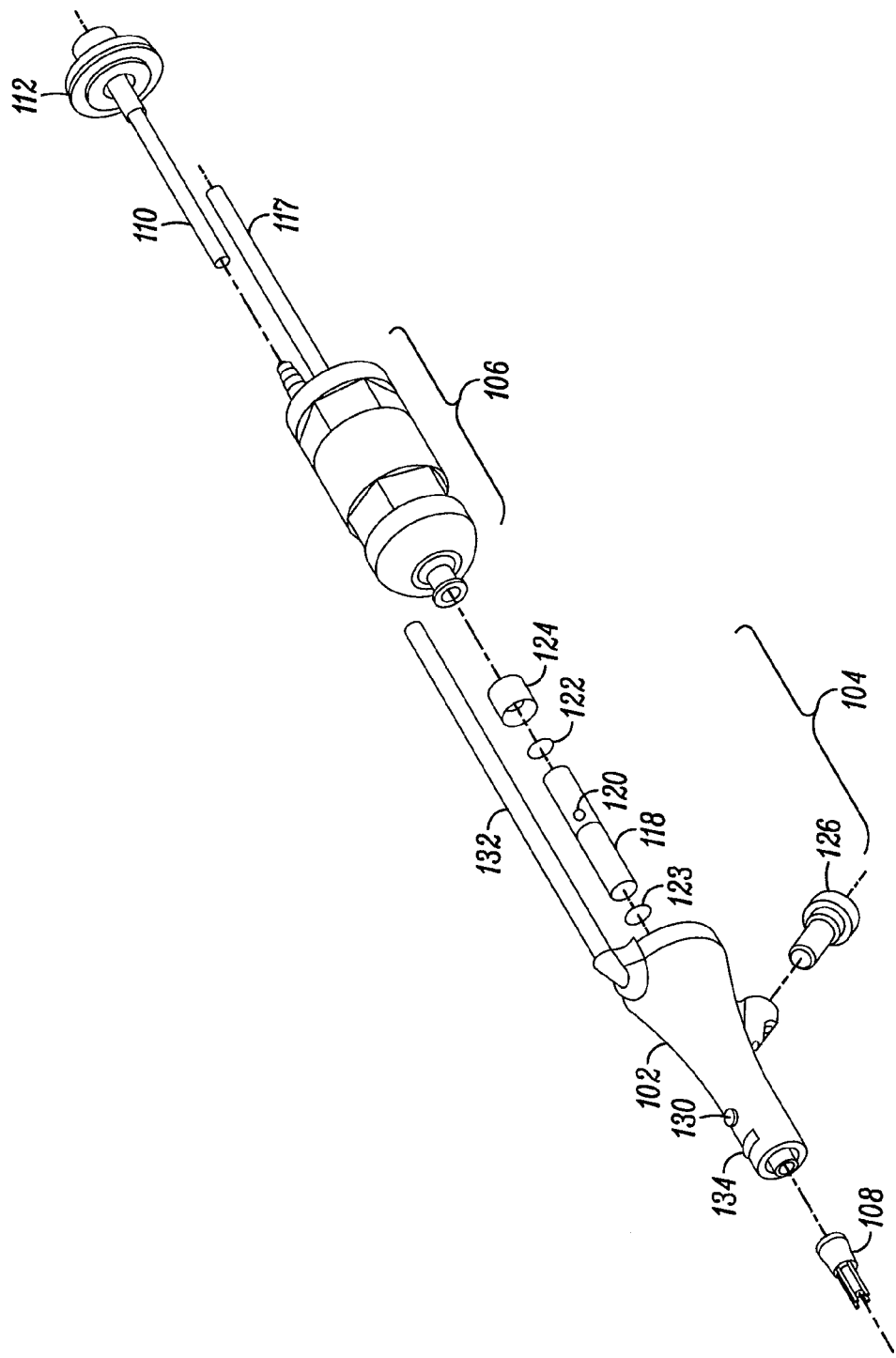
FIG. 1 is an exploded view of one implementation of a carboxy therapy applicator.
Figure 2:
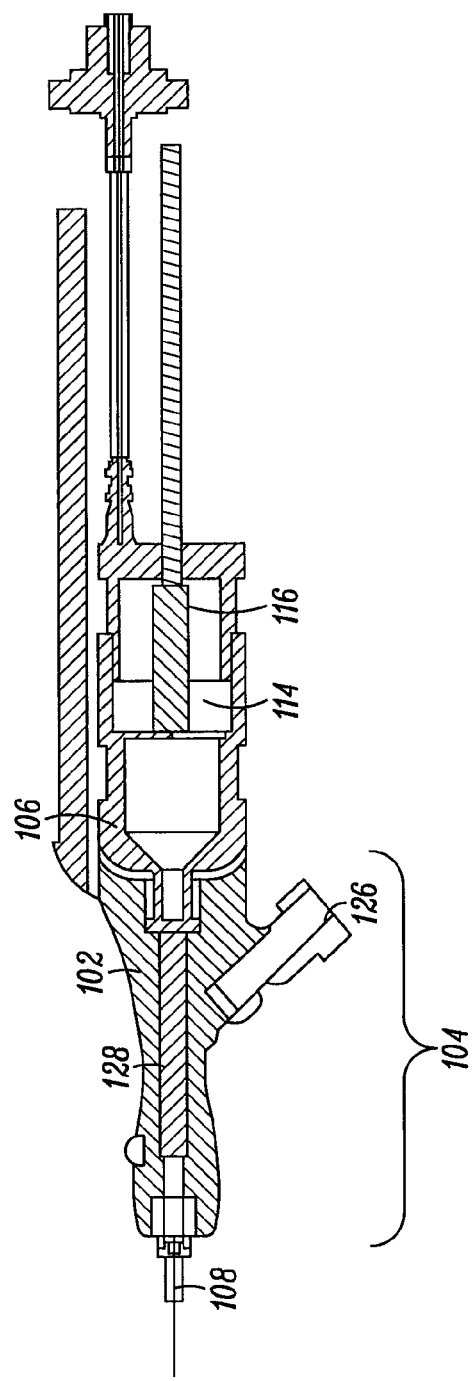
FIG. 2 is a cross-sectional view of the applicator of FIG. 1.
Figure 3:
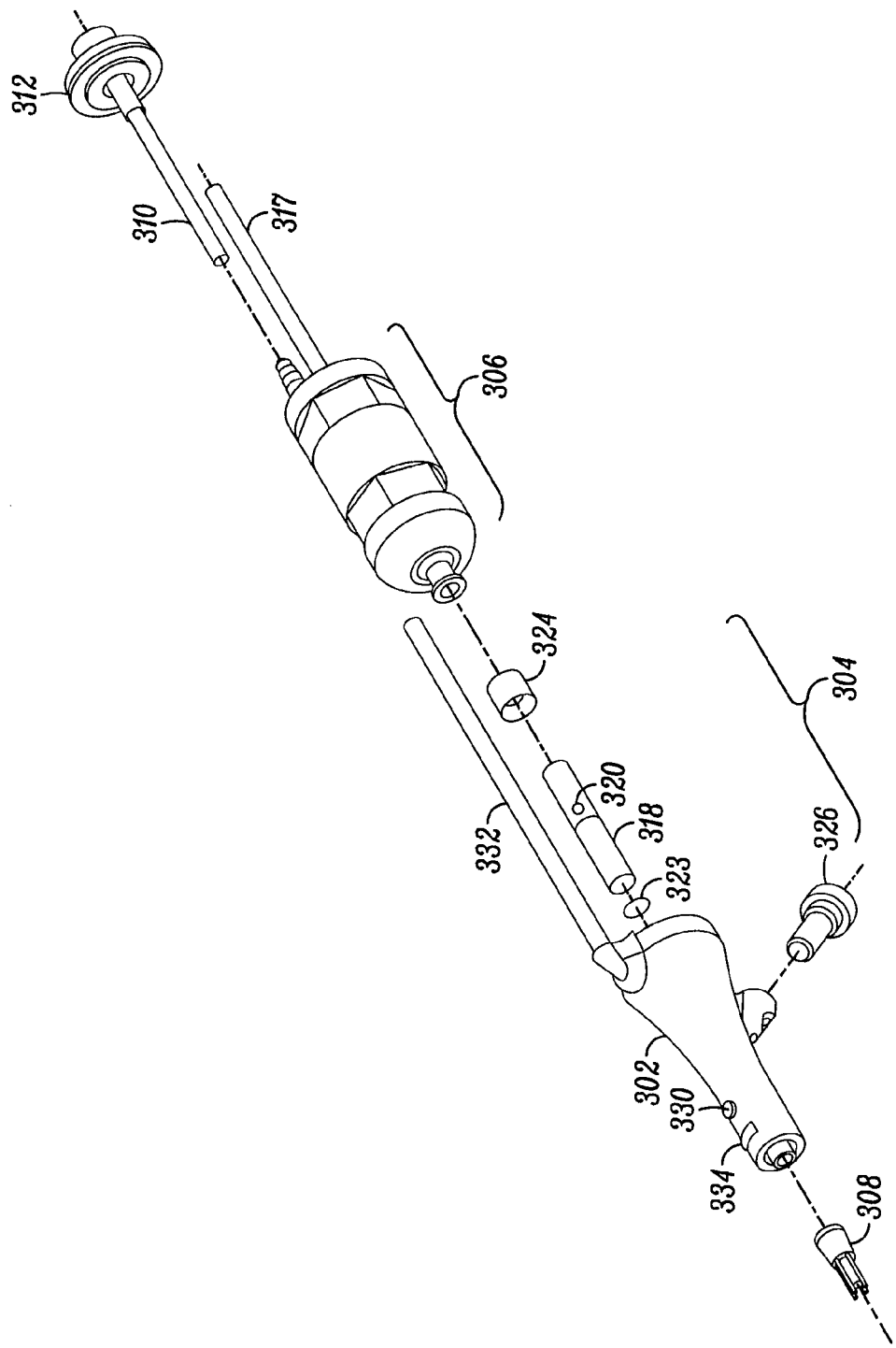
FIG. 3 is an exploded view of another implementation of a carboxy therapy applicator.
Figure 4:
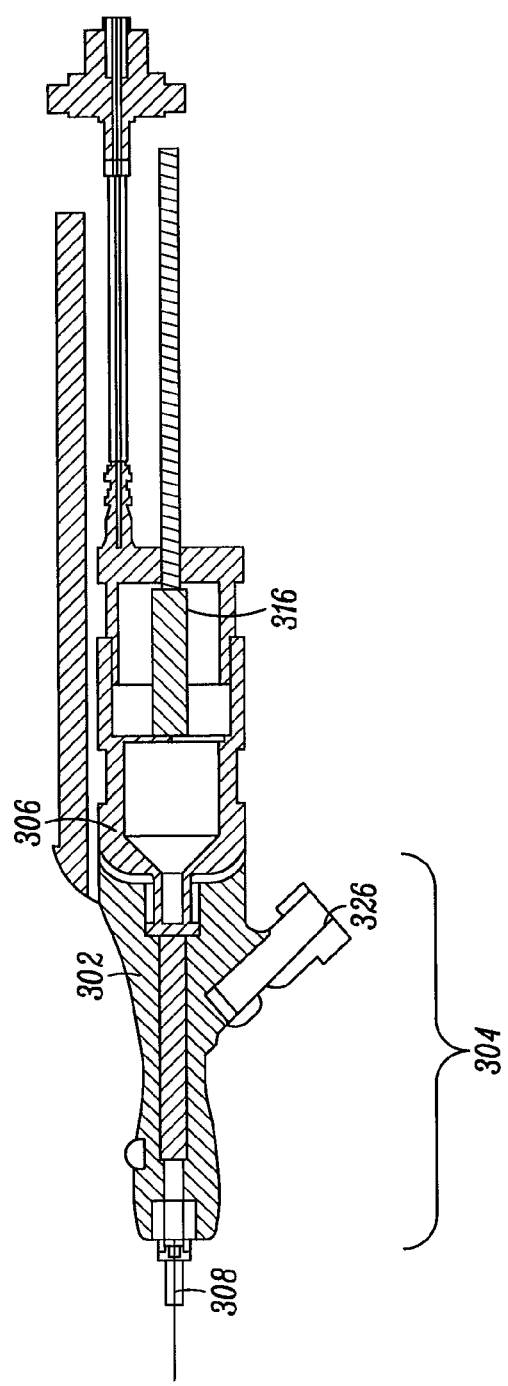
FIG. 4 is a cross-sectional view of the applicator of FIG. 3.

FIG. 1 is an exploded view of one implementation of a carboxy therapy applicator 100 and FIG. 2 is a cross-sectional view of the applicator 100 of FIG. 1. The carboxy therapy applicator 100 may include a hand piece 102, a humidification module 104, a heater module 106, and a hypodermic needle 108.

As described in more detail below, the carboxy therapy applicator 100 is configured such that the heater module 106 receives a flow of gas from a control unit, an insufflator, and/or any other gas source that may provide gas to a tubing at a predetermined pressure and/or flow rate. In some implementations the heater module 106 receives gas from a controller that is distinct from an insufflator, where in other implementations, the heater module 106 receives gas from a controller that is integrated with an insufflator. The gas is warmed in the heater module 106 and then flows into the humidification module 104 positioned in fluid communication, such as in a serial connection, with the heater module 106. Within the humidification module 104, the warmed gas is humidified before the gas flows into the hypodermic needle 108 in serial connection with the humidification module 104. The gas then flows out of the hypodermic needle 108 and into the tissue of the patient. It will be appreciated that in other implementations, rather than warming and then humidifying the gas, the gas is warmed and humidified simultaneously. Examples of general system that may be suitable to warm and humidify gas simultaneously may be found in U.S. Pat. No. 7,762,251, the entirety of which is hereby incorporated by reference.

Because the flow of gas is warmed and humidified within the carboxy therapy applicator 100 immediately before it is injected into the tissue of the patient, the carboxy therapy applicator 100 is able to provide heated, humidified gas to a patient for subcutaneous cosmetic purposes at a range of temperatures close to body temperature from 95 to 105 degrees. Providing warmed, humidified gas to the tissue of the patient reduces drying of the tissue that may cause the patient pain.

As shown in FIG. 1, gas flowing from a control unit, an insufflator, and/or another gas source may enter the heater module 106 via tubing 110 and a gas filter 112. In some implementations the gas may include carbon dioxide. However, other gases may be used. The gas may flow into the heater module 106 at a first end and flow into an interior region 114 of the heater module 106. A heater cartridge 116, that receives power from a wire 117, is positioned within the interior region 114 of the heater module 106 and warms the gas before the warmed gas exits the heater module 106 at a second end of the heater module 106. As the warmed gas exits the heater module 106, it enters the humidification module 104 that is positioned in serial connection with the heater module 106. In some implementations, the heater module 106 is threadably connected to the humidification module 104.

The humidification module 104 may include a hydrophilic filter 118, a humidification medium 120, one or more semi-permeable membranes 122, 123, a humidifier cap 124, and an injection port 126. In some implementations, the components of the humidification module 104 may be positioned within an interior region 128 of the hand piece 102.

As the warmed gas enters the humidification module, it may pass through a first semi-permeable membrane 122. The semi-permeable membrane 122 allows gas to enter the humidification module 104 while preventing other impurities and articles from entering the humidification module 104 from the heater module 106. The gas flow passes over and/or through the humidification medium 120 and absorbs moisture. In some implementations the gas flow may absorb only water vapor from the humidification medium 120, where in other implementations, the gas flow may absorb one or more other medications, chemicals, and liquids, such as sodium bicarbonate, in addition to water vapor. For example in some implementations, hydrogen peroxide ($H_2O_2$) is used with the humidification medium 120 for the purpose of adding oxygen to the gas as it passes through the humidification module 104.

Liquids may be introduced into the humidification module 104 and the humidification medium 120 using the injection port 126. In some implementations, the injection port 126 may be connected to a controller that controls the amount of liquid introduced into the humidification module 104 over a period of time.

After passing over and/or through the humidification medium 120, the gas flow passes through the hydrophilic filter 122 to filter impurities such as particulate matter or bacteria from the gas flow. Before entering the hypodermic needle 108 connected in series with the humidification module 104, the gas flow passes through a second semi-permeable membrane 123 to prevent any liquids from entering the hypodermic needle 108 from the humidification module 104 and being directly injected into a patient. The second semi-permeable membrane 123 may also serve to block any body fluids that enter the hypodermic needle 108 when inserted into human tissue from entering the humidification module 104.

In some implementations, the hypodermic needle 108 is positioned in the carboxy therapy applicator 100 immediately after the humidification module 104 so that there is no loss between the gas flow exiting the heater module 106 and the humidification module 104 and entering the hypodermic needle 108 that is penetrating the skin of the patient.

The carboxy therapy applicator 100 may include one or more switches 130 and a display 134. The one or more switches 130 allow a physician using the carboxy therapy applicator 100 to easily control the gas flow and the display 134 provides information regarding the gas flow, such as indications of a gas flow rate, a temperature of the gas within the gas flow, a pH level of the gas within the gas flow, and/or a relative humidity level of the gas within the gas flow.

In some implementations the one or more switches 130 may be membrane switches. However, it will be appreciated that other types of switches 130 may also be used. When the one or more switches 130 are membrane switches, due to the small nature of a membrane switch, multiple switches 130 may be placed on the hand piece 102 in close proximity to each other. The switches 130 may be of varying heights to create tactile differentiation between the switches 130 so that any of the one or more switches 130 may be identified by feel.

In some implementations, activation of a switch 130 may cause a signal to be sent to the control unit, insufflator, and/or other gas source to start or stop the flow of gas. In other implementations, multiple switches 130 may be used to send signals to the control unit, insufflator, and/or other gas source to increase or decrease the flow of gas. For example, a first switch 130 positioned on the hand piece 102 may create a signal to cause the control unit to increase the flow of gas and a second switch 130 positioned on the hand piece 102 may create a signal to cause the control unit to decrease the flow of gas.

In addition to controlling the flow of gas, switches 130 may also be positioned on the hand piece 102 to send a signal to the control unit, insufflator, and/or other gas source to adjust a pressure of the gas flow and/or switches 130 may be positioned on the hand piece 102 to control the temperature of the heater cartridge 116 of the heater module 106. In some implementations, switches 130 on the hand piece 102 may be used in combination to provide various control signals to the control unit, insufflator, and/or other gas source.

When activated, the switches may cause the carboxy therapy applicator 100 to send one or more control signals to the control unit, insufflator, and/or other gas source via means such as a hardwire 132 that is connected to the control unit, insufflator, and/or other gas source, or via wireless means that utilize infrared (IR) signals or radiofrequency (RF) signals to communicate with the control unit, insufflator, and/or other gas source.

It will be appreciated that by placing the switches 130 on the hand piece 102 of the carboxy therapy applicator 100, a physician is able to easily adjust important parameters for a procedure, such as gas flow, volume pressure, and gas temperature, without going back to the controller or using external applicators such as a foot pedal. By adjusting factors such as gas flow, volume pressure, and/or gas temperature, a physician is able to adjust the amount of humidification and the pH level of the gas as it is injected into the tissue of the patient.

For example, the temperature of the gas flow as it passes through the humidification module 104 affects the relative humidity of the gas. At higher temperatures, the rate (or amount) of evaporation of the liquid within the humidification module 104 is high resulting in a high relative humidity of the gas. Alternatively, at lower temperatures, the rate (or amount) of evaporation of the liquid within the humidification module 104 is low resulting in a low relative humidity of the gas.

Further, the flow rate of the gas as it passes through the humidification module 104 affects the relative humidity of the gas. The longer a unit of gas is in the humidification module 104, the more likely the unit of gas is to absorb moisture within the humidification module 104. Accordingly, increasing the gas flow rate through the humidification module 104 typically results in a decrease in the relative humidity of the gas. Alternatively, decreasing the gas flow rate through the humidification module 104 typically results in an increase in the relative humidity of the gas.

When a solution with a highly acidic pH level or a solution with a highly basic pH level is used in the humidification module 104, it will be appreciated that adjusting the gas flow or gas temperature to adjust the relative humidity of the gas will also affect the pH level of the gas. For example, when a solution with a highly acidic pH level is used in the humidification module 104, increasing the relative humidity of the gas will result in a decrease of the pH level of the gas and decreasing the relative humidity of the gas will result in an increase of the pH level of the gas. Similarly, when a solution with a highly basic pH level is used in the humidification module 104, increasing the relative humidity of the gas will result in an increase in the pH level of the gas and decreasing the relative humidity of the gas will result in a decrease of the pH level of the gas.

For example, when the relative humidity of a gas flow containing carbon dioxide is increased, carbon dioxide will often break down into carbonic acid. As discussed above, the formation of carbonic acid is human tissue can result in increased cellular activity and/or increased pain to a patient. In order to decrease the level of acidity when the gas flow is injected into the tissue of the patient and decrease the likelihood of carbonic acid forming in the tissue, solutions with different pH levels may be introduced into the humidification medium. In some implementations, solutions comprising between 7.5% sodium bicarbonate and 8.4% sodium bicarbonate may be used to decrease the acidity level of the gas.

In some implementations, the applicator 100 or the control box may include a pressure safety valve positioned between the humidification module 104 and the hypodermic needle 108. The pressure safety valve prevents any over pressurization by providing pressure relief at the terminus of the connection to the hypodermic needle 108. In some implementations, the pressure safety valve may control the pressure in the sub-dermal pouch to a range from 1 mmHg to 150 mmHg, with an optimal range, depending on the location of the body, of between 1 mmHg and 50 mmHg, and flow rates from 1 ml per minute to 500 ml per minute.

In some implementations, the applicator 100 may further include a carbon dioxide detector configured to monitor carbon dioxide levels of the area around a patient and physician. Side effects of carbon dioxide may include drowsiness, confusion, nausea, and create the potential for adverse conditions for the physician or patient. The applicator may monitor the area to determine if carbon dioxide levels, either generated from the procedure, the equipment, or leaks from the carbon dioxide source, are large enough to create a hazard in the working environment, and indicate a potential hazard on the display 134 of the applicator.

Further implementations of carboxy therapy applicators are illustrated in FIGS. 3-14. In the implementation illustrated in FIGS. 3 and 4, the humidification module 304 includes a semi-permeable membrane 322 positioned to block liquids from flowing into the hypodermic needle 308. However, the implementation does not include a semi-permeable membrane positioned between the humidification module 304 and the heater module 306.

Figure 5:
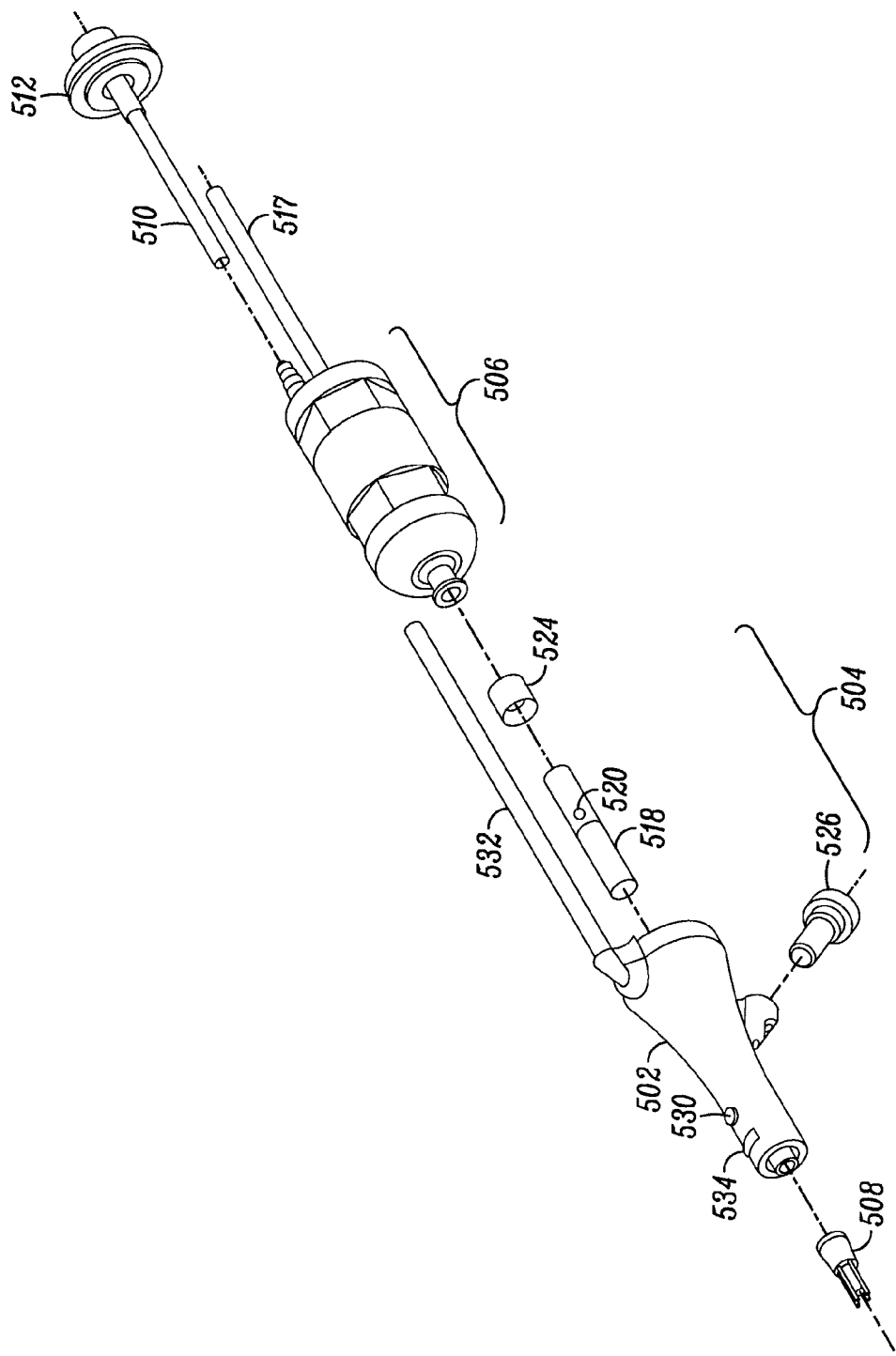
FIG. 5 is an exploded view of another implementation of a carboxy therapy applicator.
Figure 6:
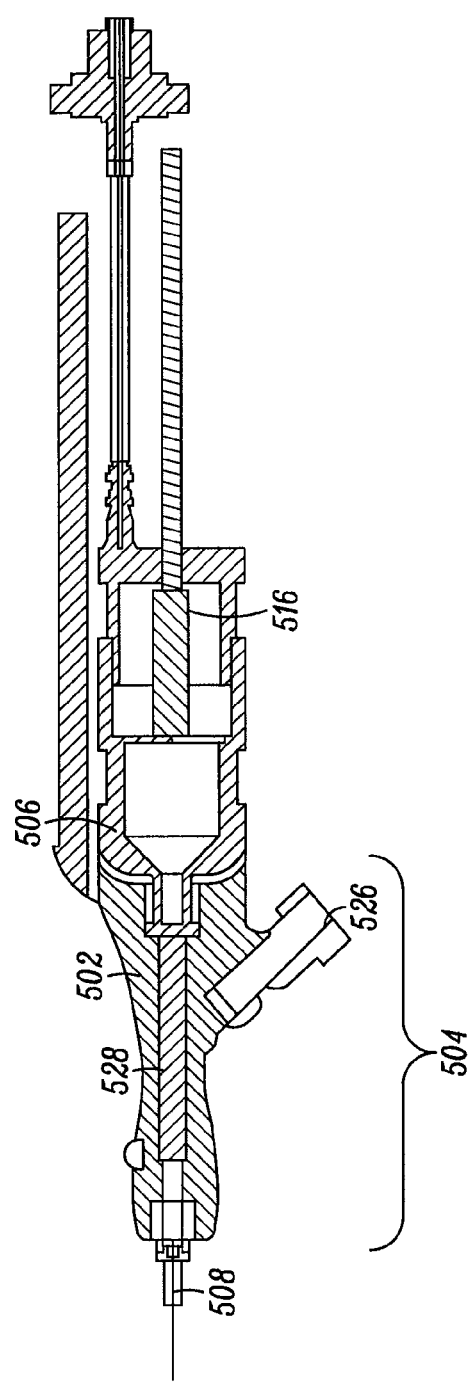
FIG. 6 is a cross-sectional view of the applicator of FIG. 5.

In the implementation illustrated in FIGS. 5 and 6, the humidification module 504 does not include a semi-permeable membrane positioned to block liquids from flowing into the hypodermic needle 508. The implementation also does not include a semi-permeable membrane positioned between the humidification module 504 and the heater module 506.

Figure 7:
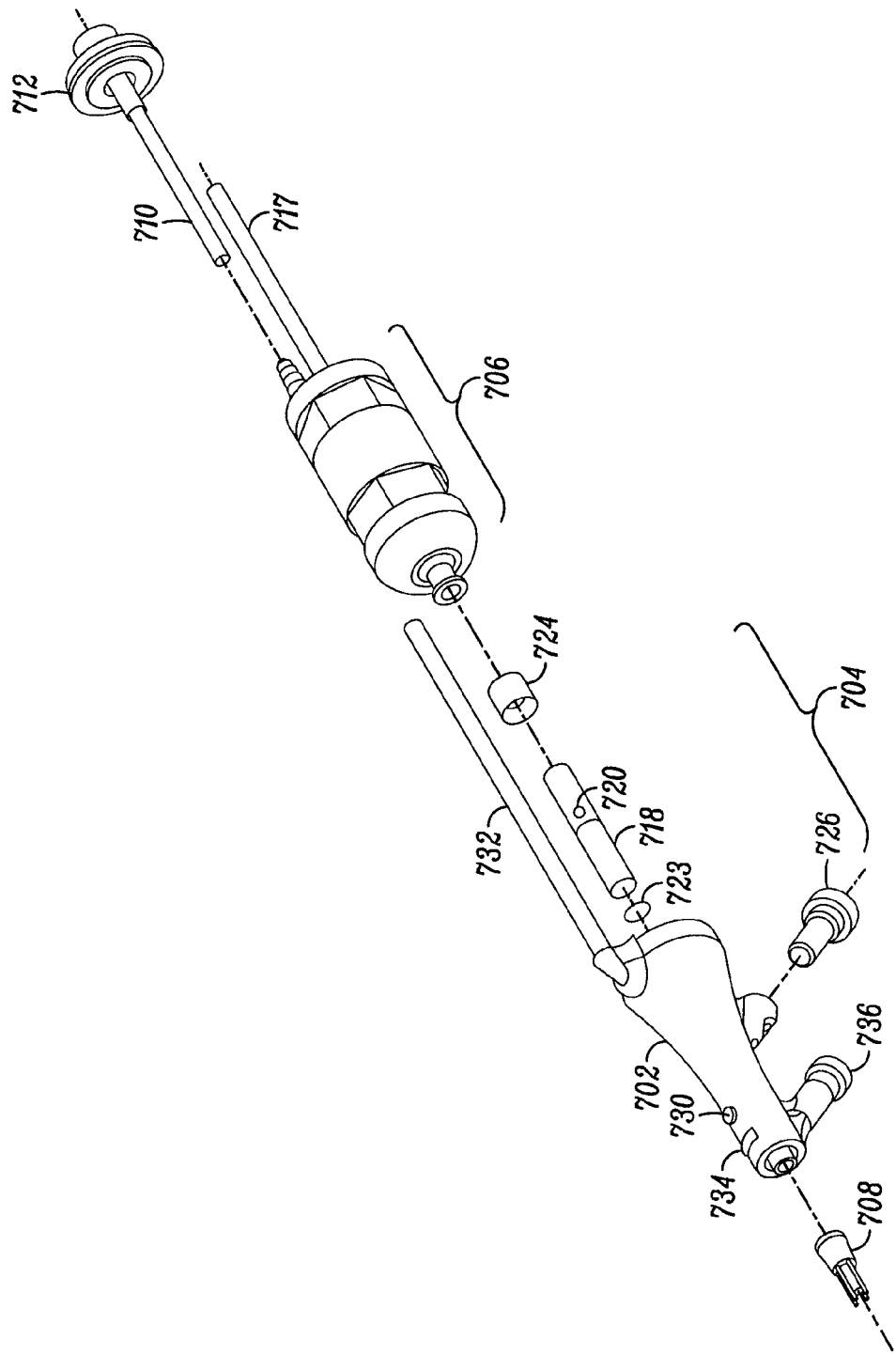
FIG. 7 is an exploded view of another implementation of a carboxy therapy applicator.
Figure 8:
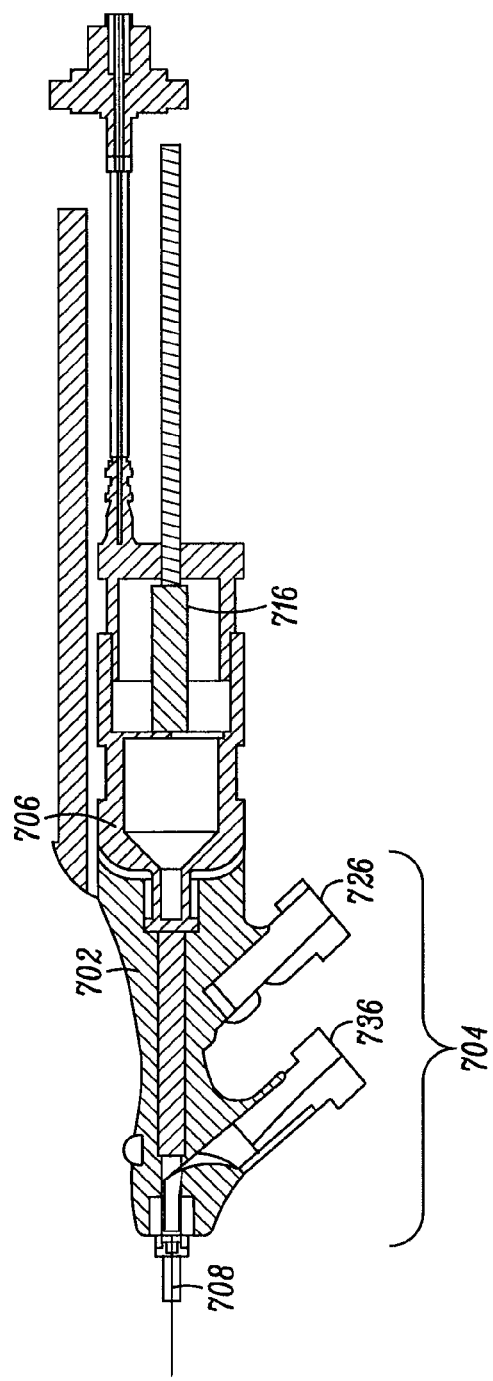
FIG. 8 is a cross-sectional view of the applicator of FIG. 7.

In the implementation illustrated in FIGS. 7 and 8, the carboxy therapy applicator includes one or more aerosol ports 736. Each aerosol port 736 is configured to allow a physician to insert an aerosolized medicament such as anti-inflammatories or pain medication into the gas flow. The aerosolized port 736 is typically positioned in the applicator such that the aerosolized medicament is inserted into the gas flow shortly before the gas flows into the hypodermic needle 708. However, the aerosolized port 736 may be positioned at other locations in the applicator to insert an aerosolized medicament into the gas flow.

Figure 9:
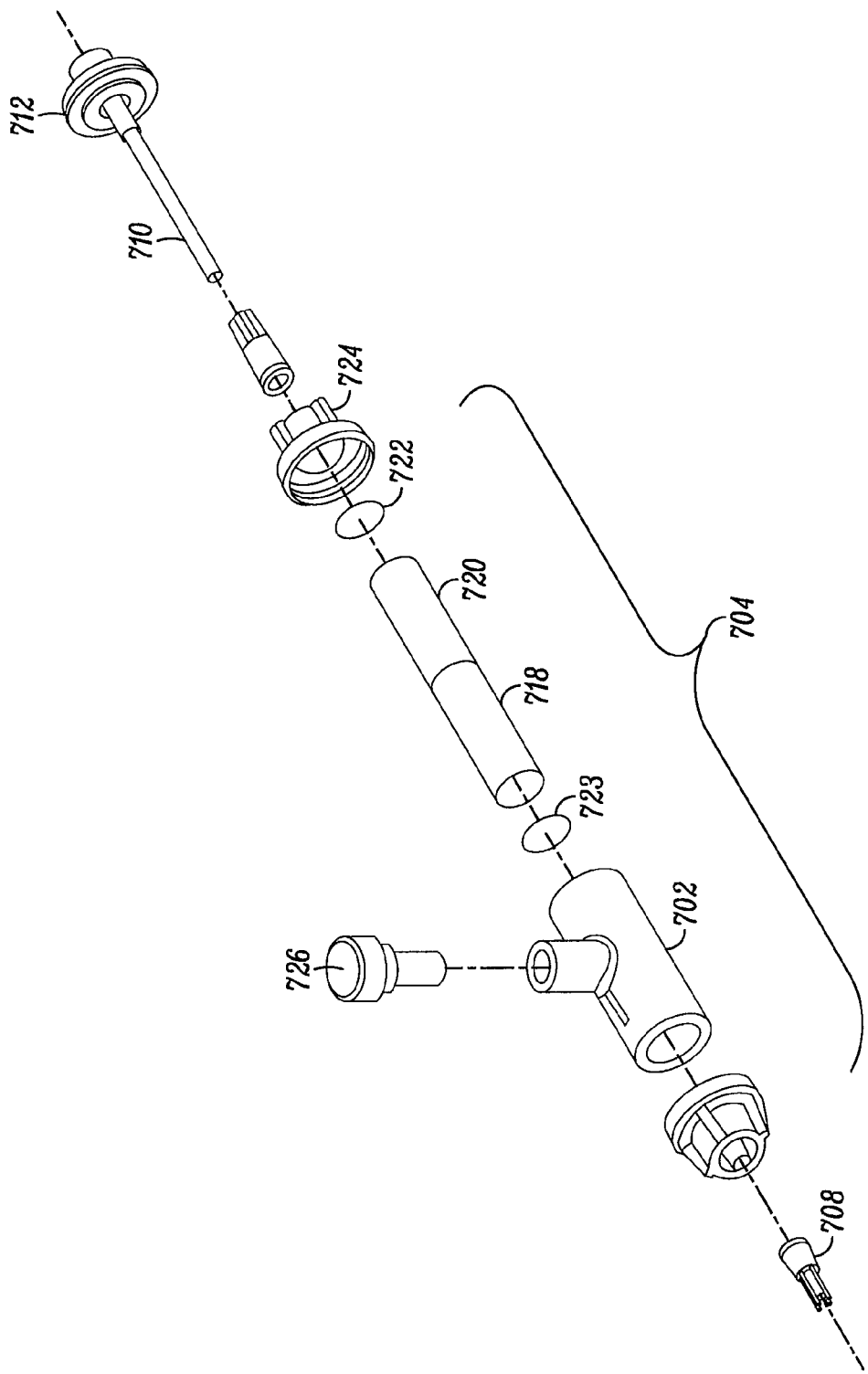
FIG. 9 is an exploded view of another implementation of a carboxy therapy applicator.
Figure 10:
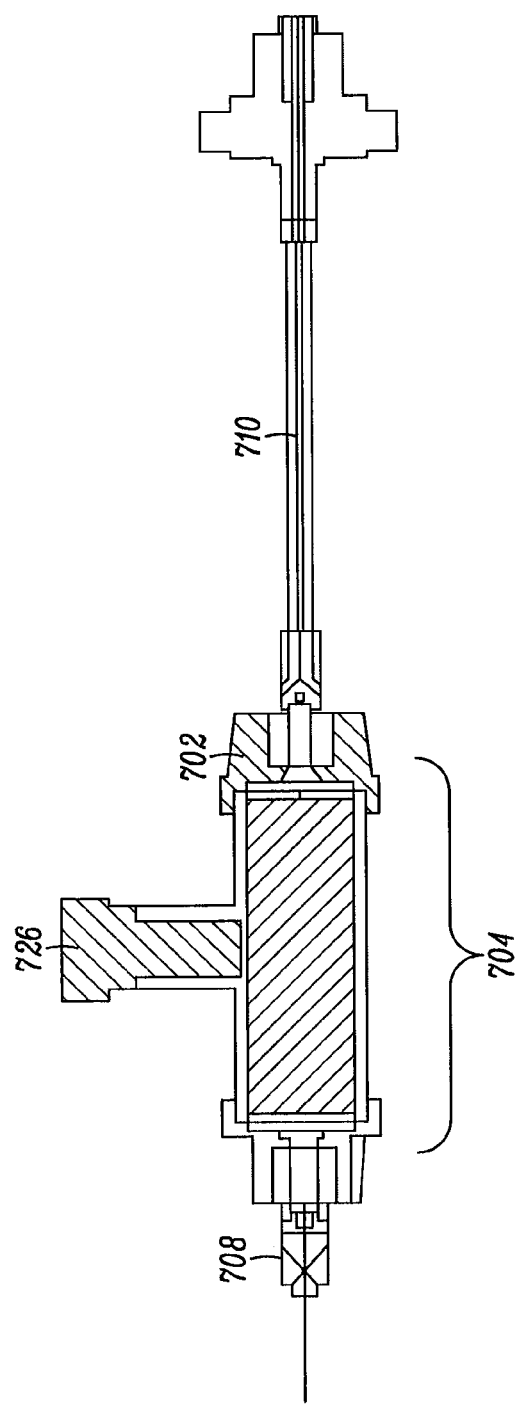
FIG. 10 is a cross-sectional view of the applicator of FIG. 9.

In the implementation illustrated in FIGS. 9 and 10, the applicator does not include a heater module. Instead, the gas flows from the control unit directly into the humidification module 704. After absorbing moisture within the humidification module 704, the gas flows into the hypodermic needle 708 for insertion into the tissue of the patient.

Figure 11:
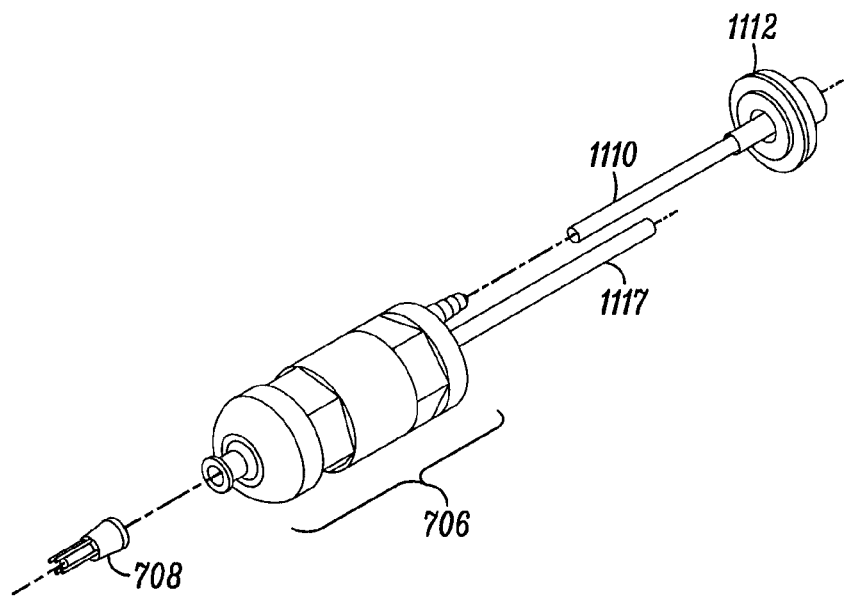
FIG. 11 is an exploded view of another implementation of a carboxy therapy applicator.
Figure 12:
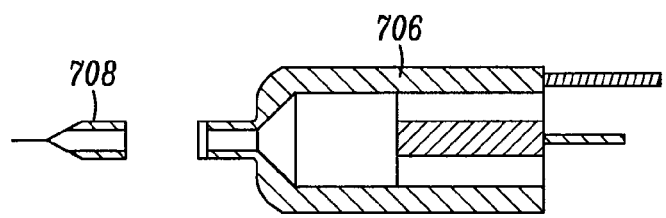
FIG. 12 is a cross-sectional view of the applicator of FIG. 11.

In the implementation illustrated in FIGS. 11 and 12, the applicator does not include a humidification module. Instead, the hypodermic needle 1108 is serially connected to the heater module 1106. Accordingly, after the gas is heated within the heater module 1106, the gas flows into the hypodermic needle 1108 for insertion into the tissue of the patient. In these implementation, the applicator may include a port such as those described above that are configured to receive water vapor, liquids, aerosolized medicaments, and/or chemical, and insert the received substance into the gas flow before the gas flows into the hypodermic needle 1108.

Figure 13:
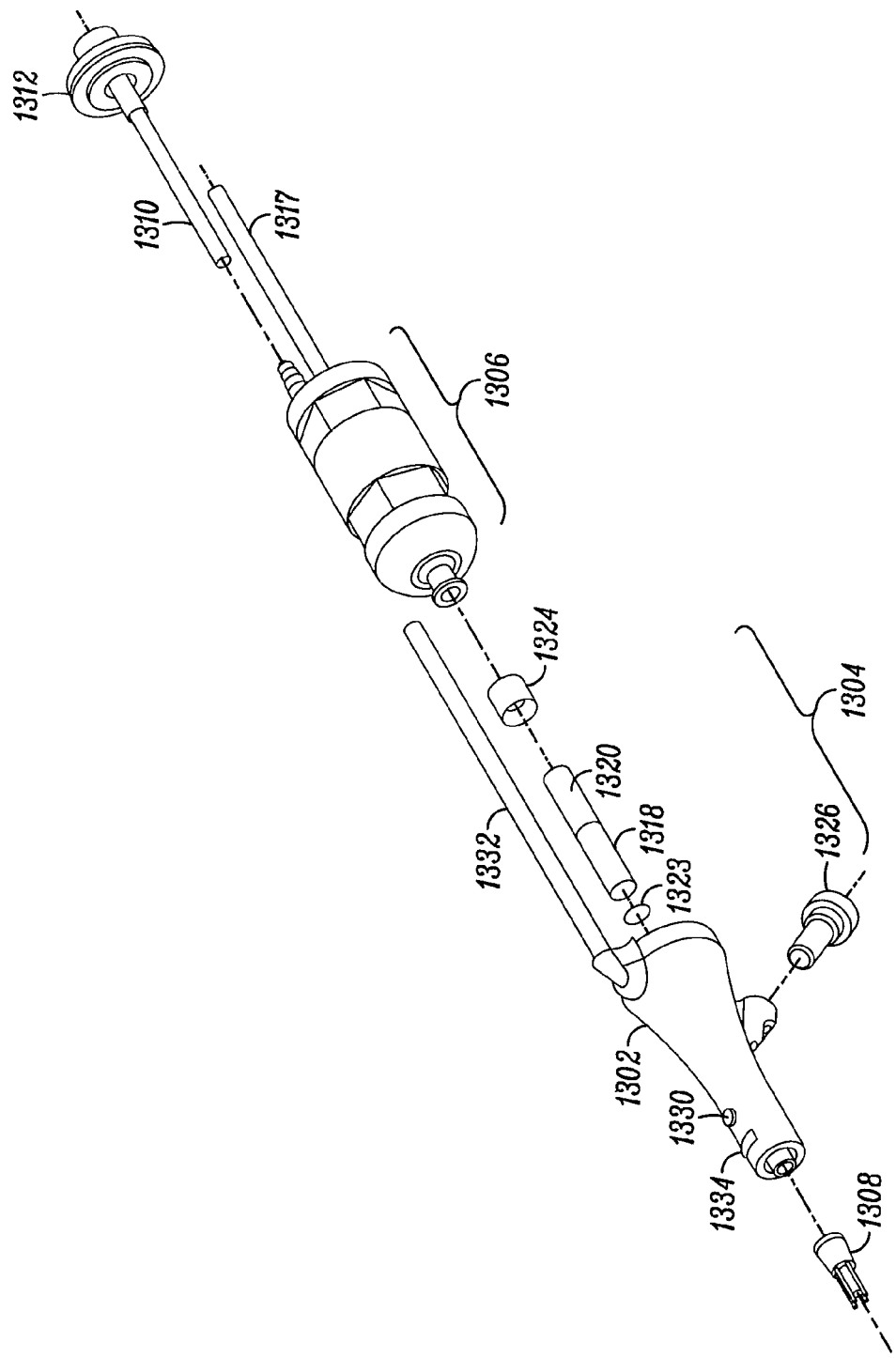
FIG. 13 is an exploded view of another implementation of a carboxy therapy applicator.
Figure 14:
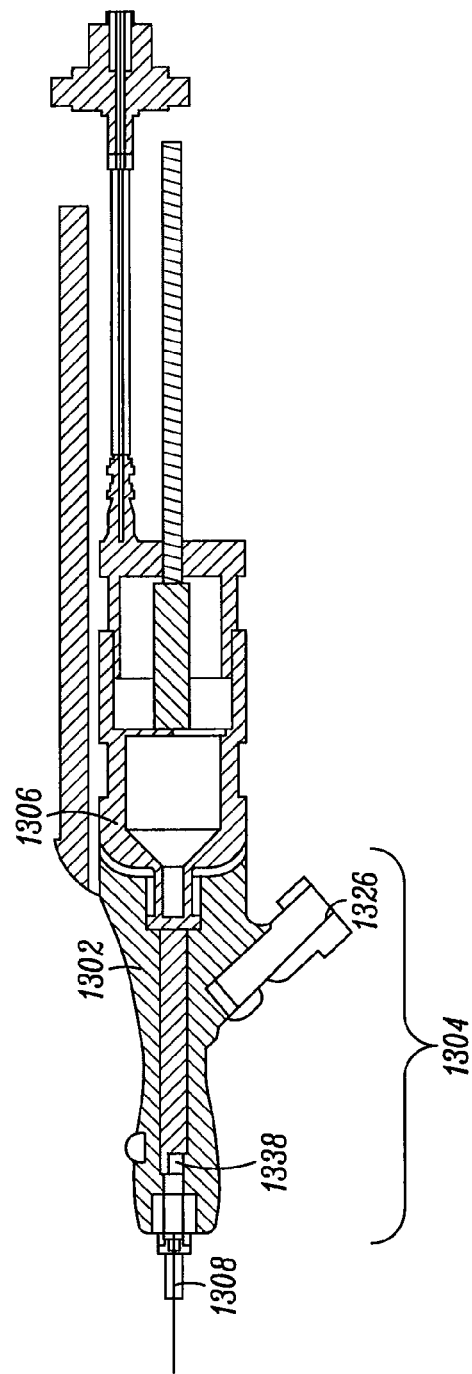
FIG. 14 is a cross-sectional view of the applicator of FIG. 13.

In the implementation illustrated in FIGS. 13 and 14, the applicator includes a sensor 1338 to measure a property of the gas before it enters the hypodermic needle 1308. For example, the sensor 1338 could be used to measure one or more of the relative humidity of the gas, the temperature of the gas, the pressure of the gas, the flow rate of the gas, the pH level of the gas, or the carbon dioxide level of the gas. In some implementations, information regarding the property of the gas detected by the sensor 1338 is provide on the display 1334 of the applicator.

Figure 15:
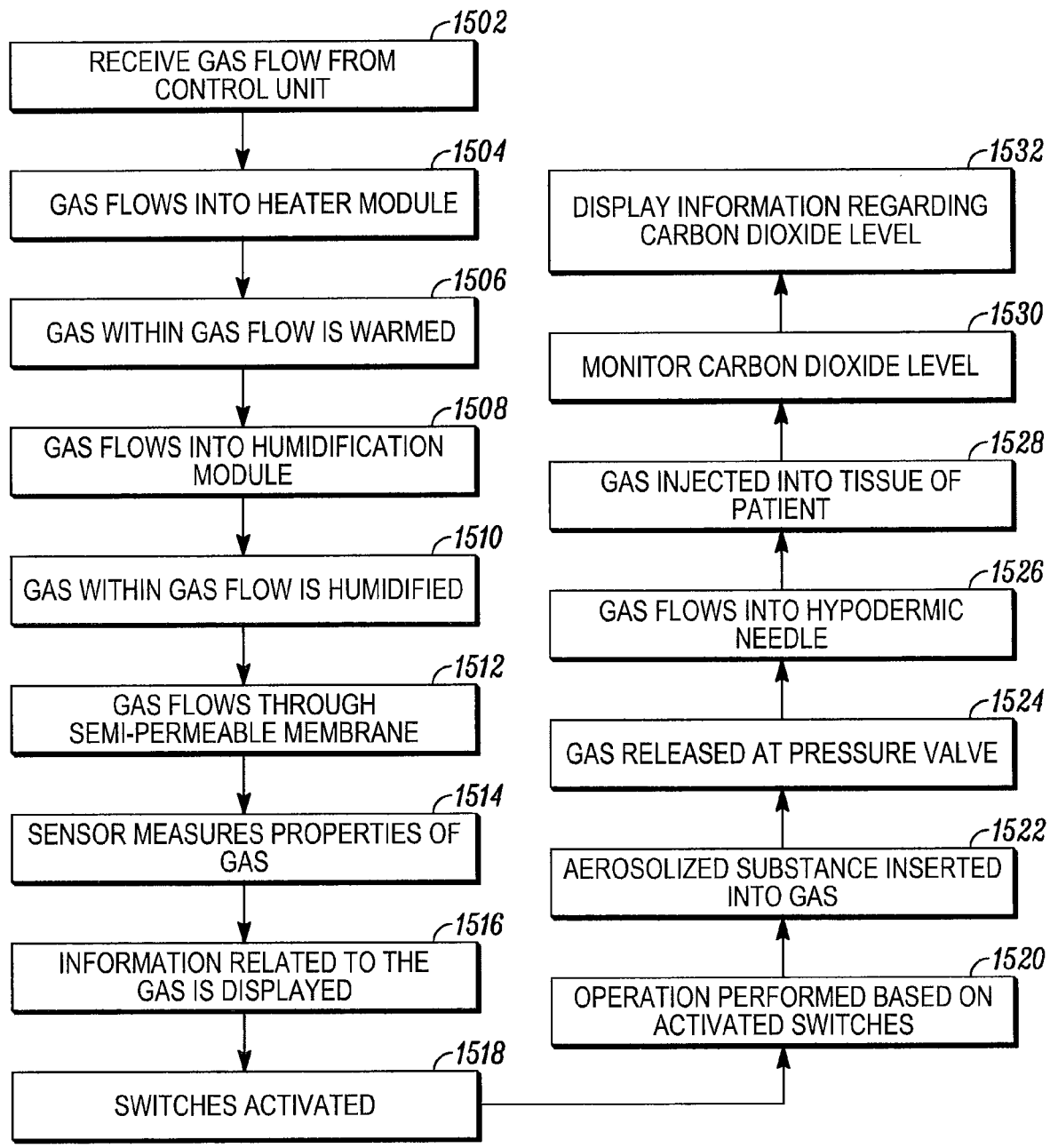
FIG. 15 is a flow chart of a method for performing carboxy therapy.

FIG. 15 is a flow chart of a method for providing carboxy therapy to a patient using implementations of the carboxy therapy applicator described above. The method begins at 1502 with the carboxy therapy applicator receiving a gas flow from a controller, an insufflator, and/or another gas source. In some implementations the gas comprises carbon dioxide. However, in other implementations the gas may comprise other types of gases or combination of gases in various percentages. One example of a mixed-gas insufflator system that may be used with the present application is described in U.S. Pat. No. 7,654,975, the entirety of which is hereby incorporated by reference.

At step 1504, the gas flows into a heater module of the applicator and is warmed at step 1506. The warmed gas flows out of the heater module of the applicator and into a humidification module 1508. Within the humidification module, the gas flows over and/or through a humidification medium and absorbs moisture at step 1510. In some implementations, the gas absorbs water vapor only as the gas flows over and/or through the humidification medium, where in other implementations, the gas absorbs water vapor and other medicaments such as sodium bicarbonate as it flows over and/or through the humidification medium. After absorbing moisture, the gas flows through a semi-permeable membrane at step 1512 to block liquids from exiting the humidification module.

At step 1514, a sensor in the carboxy therapy applicator measures one or more properties of the gas, and at step 1516, information relating to the one or more properties measured by the sensor is displayed on a display of the carboxy therapy applicator. In some implementations the sensor may measure properties of the gas such as the relative humidity of the gas, the temperature of the gas, pressure of the gas, the flow rate of the gas, the pH level of the gas, or the carbon dioxide level of the gas.

At step 1518, a physician may activate one or more switches on the carboxy therapy applicator. In response, at step 1520, the carboxy therapy applicator may perform operations based on the activated switches such as sending a signal to a control unit to start a gas flow, stop a gas flow, decrease a flow rate of the gas, increase a flow rate of the gas, increase a pressure of the gas, or decrease a pressure of the gas. The carboxy therapy applicator may additionally perform actions based on the activated switches such as increasing or decreasing a temperature of a heating cartridge of the heating module of the carboxy therapy applicator to change a temperature of the gas flowing through the applicator.

At step 1522, an aerosolized substance or a liquid may be inserted into the gas flow via a port in the applicator. The aerosolized substance or liquid may be water vapor, an aerosolized medicament, a substance to change a pH level of the gas, or any other substance that a physician may wish to insert into the gas flow before the gas is injected into a tissue of the patient.

The gas may flow across a pressure valve at step 1524, where the pressure valve may release gas from the carboxy therapy applicator when the pressure of the gas flow exceeds a predetermined threshold.

At step 1526, the gas flows into a hypodermic needle of the applicator, and at step 1528, the gas is injected into a tissue of a patient. At step 1530, a carbon dioxide sensor may monitor a carbon dioxide level around the patient and the physician, and at step 1532, information from the carbon dioxide sensor is provided on the display of the applicator.

Figure 16:
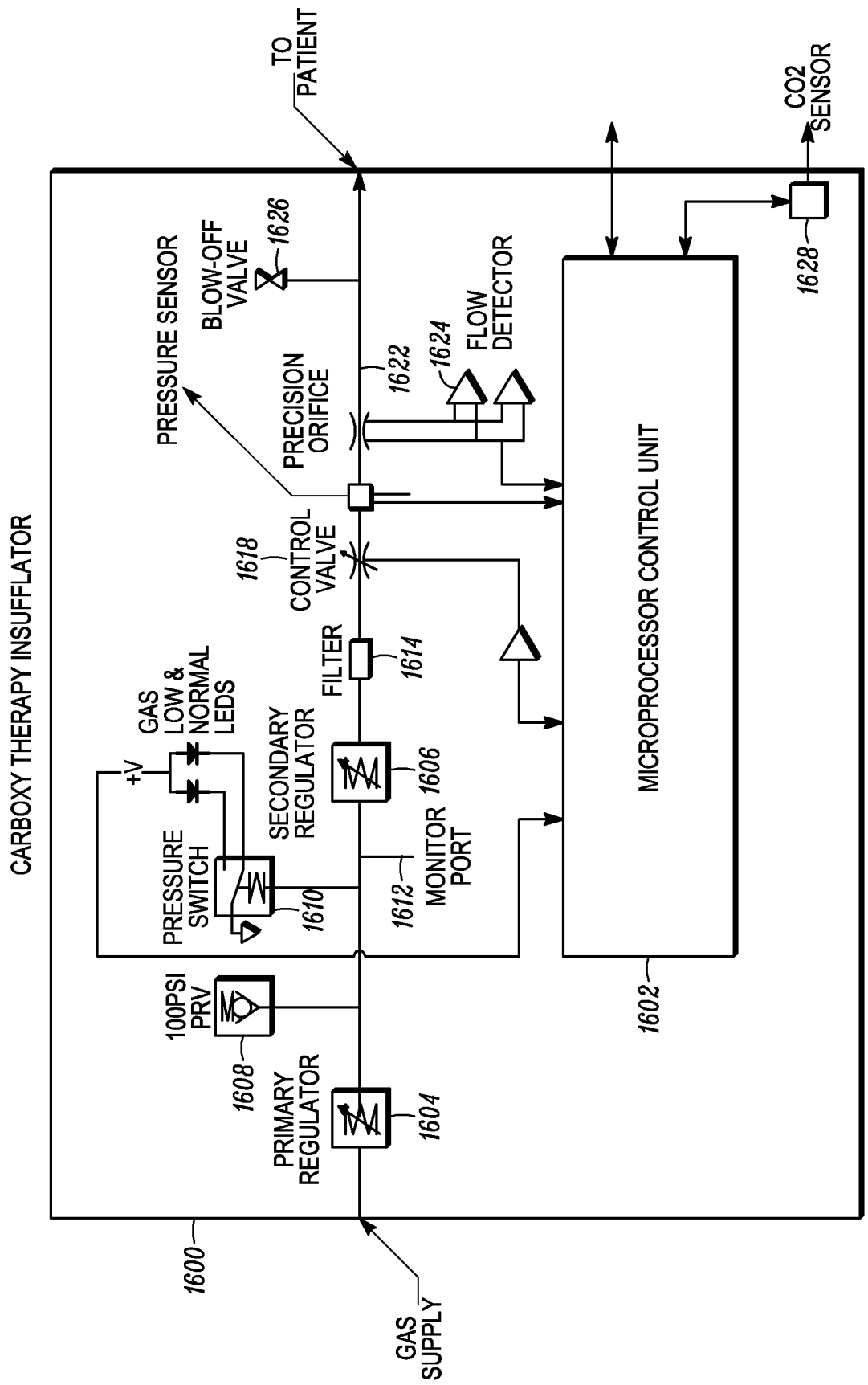
FIG. 16 is a diagram of a controller that may be used in carboxy therapy.

FIG. 16 is a diagram of a controller 1600 that may be used in carboxy therapy. While the controller 1600 illustrated in FIG. 16 may be shown as part of a gas delivery apparatus, such as an insufflator, it should be appreciated that in other implementations the controller 1600 may be distinct from the gas delivery apparatus and be located in a control box, one of the carboxy therapy applicators described above with respect to FIGS. 1-15, or in any other part of the gas delivery system.

Traditional laparoscopic insufflators are generally high flow rate, pressure controlled devices. However, in dermatological applications, it is desirable to control a flow rate, pressure, and volume of subcutaneous injection of a gas such as $CO_2$. Further, due to the use of needles in carboxy therapy that are typically smaller in size, on the order of approximately 28 to 30 gauge, than those utilized with traditional laparoscopic insufflators, the need to control flow rates, volume, and pressure of a gas is more significant than in traditional laparoscopic insufflators.

During operation, the controller 1600 measures and adjusts a flow rate, pressure, and/or volume of a gas to account for variations in tissue and a desired affect of the injected gas. For example, subcutaneous injection of gas for wrinkle applications may require control of small amounts of gas volume (as low as 5 ml) at relative flow rates between 5 to 20 ml per minute, and at a pressure of between 5 to 30 mmHg. The controller may monitor and adjust the flow rate, pressure, and/or volume of a gas to stay within these parameters.

The controller 1600 of FIG. 16 includes a microprocessor control unit 1602, a primary regulator 1604, a secondary regulator 1606, a pressure release valve 1608, a pressure switch 1610, a monitor port 1612, a filter 1614, a control valve 1618, a pressure sensor 1620, a precision orifice 1622, a flow detector 1624, and a blow-off valve 1626. However, it will be appreciated that in other implementations, the controller 1600 may not include all elements shown in FIG. 16.

In some implementations, the microprocessor control unit 1602 may be in communication with the pressure switch 1610, the control valve 1618, the pressure sensor 1620, the precision orifice 1622, and the flow detector 1624, as well as a carboxy applicator such as one of the applicators described above with respect to FIGS. 1-15. The controller 1600 utilizes the microprocessor control unit 1602 to control flow rate, pressure, and/or volume of a gas flow through the use of the variable control valves and orifices, pressure sensing sensors, and a timed sequence of valve activation to allow for the selection of a volume amount, a flow rate, and a not to exceed pressure.

For example, controller 1600 may operate the control valve 1618 to be alternatively open and closed to allow the flow path to equalize for the purpose of taking a pressure reading, and then reopening to fulfill the desired selected volume. Because of the severe restriction caused by the small gauge needles required for procedures such as carboxy therapy, the pressure measurements require longer delays to allow for proper settling time. In this instance, the delay time is greater than 250 microseconds, as compared to endoscopic insufflator controllers that are generally significantly less than 250 microseconds.

The controller 1600 may further include a $CO_2$ detector 1628 in communication with the microprocessor control unit 1602 that can monitor a level of $CO_2$ gas at an operative area such as a working environment. As more procedures using insufflation and $CO_2$, such as laparoscopy, virtual colonoscopy, endoscopy, and carboxy therapy, move out of an operating room environment, the work environments where insufflation and $CO_2$ are used may not be optimized for proper air exchange to prevent a buildup of $CO_2$ in a location where a procedure is performed. The effects of exposure to $CO_2$ may include drowsiness, confusion, and nausea, and create the potential for adverse conditions for an operator performing a procedure or a patient that is receiving the procedure. The controller 1600 may also include the $CO_2$ detector 1628 to monitor a working environment where a procedure using $CO_2$ is performed to determine if $CO_2$ levels, either generated from the procedure, the equipment, or leaks from the $CO_2$ source, are large enough to create a hazard in the working environment, and indicate a potential hazard.

FIGS. 1-15 illustrate various implementations and methods for a carboxy therapy applicator to provide warmed, humidified gas to a patient for subcutaneous cosmetic purposes. Additionally, the disclosed carboxy therapy applicators provide a physician the ability to easily control parameter of gas flow, gas pressure, gas temperature, and pH level directly from the applicator. FIG. 16 illustrates a diagram of a controller that may be used in carboxy therapy in conjunction with a gas delivery apparatus, such as an insufflator, and an applicator such as those described in conjunction with FIGS. 1-15.

The embodiments of the invention disclosed herein are presently considered to be preferred, various changes and modifications can be made without departing from the spirit and scope of the invention. As noted, the discussion above is descriptive, illustrative and exemplary and is not to be taken as limiting the scope defined by any appended claims, and all changes that come within the meaning and range of equivalents are intended to be embraced therein.

What is claimed is:

1. A method for monitoring and controlling a flow of gas within a handheld carboxy therapy applicator, the method comprising:
   reading a flow rate pressure and a volume of gas flow through the handheld carboxy therapy applicator with a pressure sensor and a flow detector positioned in the handheld carboxy therapy applicator; and
   automatically controlling, with a microprocessor control unit positioned in the handheld carboxy therapy applicator, a flow rate, pressure, and volume of the gas flow through the handheld carboxy therapy applicator based on the reading of the flow rate pressure and the volume of gas through the handheld carboxy therapy applicator.

2. The method of claim 1, further comprising:
   measuring, with a carbon dioxide detector positioned on the handheld carboxy therapy applicator, a level of carbon dioxide where carboxy therapy is applied to a patient with the handheld carboxy therapy applicator; and
   adjusting, with the microprocessor control unit, one or more of the flow rate, pressure, and volume of the gas flow through the handheld carboxy therapy applicator based on the level of carbon dioxide.

3. The method of claim 1, wherein the microprocessor control unit is configured to control the flow rate of the gas flow to be between 1 ml per minute to 500 ml per minute.

4. The method of claim 1, wherein the microprocessor controller is configured to control a pressure in a sub-dermal pouch to be between a range of between 1 mmHg to 150 mmHg.

5. The method of claim 1, further comprising:
   receiving, at a microprocessor control unit, a signal from a switch positioned on the handheld carboxy therapy applicator to increase a flow of gas through the handheld carboxy therapy applicator; and
   increasing the flow of gas through the handheld carboxy therapy applicator, with the microprocessor control unit, in response to receipt of the signal from the switch.

6. The method of claim 1, further comprising:
   receiving, at a microprocessor control unit, a signal from a switch positioned on the handheld carboxy therapy applicator to decrease the flow of gas through the handheld carboxy therapy applicator; and
   decreasing a flow of gas through the handheld carboxy therapy applicator, with the microprocessor control unit, in response to receipt of the signal from the switch.

7. The method of claim 1, further comprising:
   receiving a flow of gas in the handheld carboxy therapy applicator of a gas volume as slow as 5 ml at a relative flow rate of between 5 to 20 ml per minute, and at a pressure of between 5 to 30 mmHg per minute.

8. The method of claim 1, further comprising:
   controlling, with the microprocessor control unit, a control valve within the handheld carboxy therapy applicator to alternatively open and close the control valve to allow a flow of gas to equalize; and
   controlling, with the microprocessor control unit, the flow rate pressure sensor to measure a pressure of the flow of gas while the flow of gas is equalized.

9. The method of claim 8, wherein the microprocessor measures the pressure of the flow of gas with the flow rate pressure sensor at intervals of greater than 250 microseconds.

* * * * *